United States Patent [19]

Dinerstein et al.

[11] Patent Number: 5,223,518

[45] Date of Patent: Jun. 29, 1993

[54] 1-PHENYL-3-ARYL-2-PROPYNE-1-ONE USEFUL AS CALCIUM UPTAKE INHIBITORS

[75] Inventors: Robert J. Dinerstein, Cincinnati; Jeffrey S. Sabol, Loveland; Keith A. Diekema, West Chester, all of Ohio

[73] Assignee: Merrell Dow Pharmaceuticals Inc., Cincinnati, Ohio

[21] Appl. No.: 892,624

[22] Filed: Jun. 1, 1992

Related U.S. Application Data

[63] Continuation of Ser. No. 595,506, Oct. 11, 1990, which is a continuation-in-part of Ser. No. 585,411, Sep. 20, 1990, abandoned.

[51] Int. Cl.$^5$ ............... A61K 31/44; C07D 213/46; C07D 213/73; C07D 213/74
[52] U.S. Cl. .................... 514/345; 514/351; 514/357; 546/300; 546/301; 546/302; 546/312; 546/334; 546/340
[58] Field of Search ............ 546/340, 334, 312, 300, 546/301, 302; 514/345, 351, 357

[56] References Cited

U.S. PATENT DOCUMENTS 3,409,424  11/1968  Brewbaker et al. ............ 71/70
4,929,741  5/1990  Fischli et al. ............... 549/447

OTHER PUBLICATIONS

Gerko, V. I., et al. Opt Spektrosk 45(1), 203–5 (1978); Physical Chem. 89, 146012q.
Jong, T. T., et al., Chem. Soc., Perkin Trans. 1(2), 423–4 (1990); Chem. Abst. 113,97350b.
Chen, F., et al., Tai-Wan K'o Hsueh 26(3–4), 98–9 (1972); Chem. Abst., 78(23), 147754t, Jun. 11, 1979.
Durinda, J., et al., Cesk. Farm. 26(5), 140–9 (1977); Chem. Abst. 88(1), 6671h, Jan. 2, 1978.
Boedeker, J., et al., J. Prakt. Chem. 324(1), 15–20 (1982); Chem. Abst. 97(3), 23594p, Jul. 19, 1982.
Sacchar, S. P., et al., Bokin Bobai 11(5), 269–74 (1983); Chem. Abst. 99(7), 139709A, Oct. 24, 1983.
Minn, K., 8th Int. Conf. on Organic Synthesis (IUPAC), Helsinki, 23–27 Jul. 1990.

*Primary Examiner*—Alan L. Rotman
*Attorney, Agent, or Firm*—Kenneth J. Collier

[57] ABSTRACT

This invention relates to 1-phenyl-3-aryl-2-propyne-1-ones, the use of these compounds as calcium uptake inhibitors in leukocytes and thrombocytes, and pharmaceutical compositions containing these compounds as active ingredients, and the process of their preparation.

9 Claims, No Drawings

1-PHENYL-3-ARYL-2-PROPYNE-1-ONE USEFUL AS CALCIUM UPTAKE INHIBITORS

FIELD of the INVENTION

This is a continuation of application Ser. No. 07/595,506, filed Oct. 11, 1990, continuation-in-part of application Ser. No. 07/585,411, filed on Sep. 20, 1990 now abandoned. This invention relates to 1-phenyl-3-aryl-2-propyne-1-ones, the use of these compounds as calcium uptake inhibitors in leukocytes and thrombocytes, and pharma-ceutical compositions containing these compounds as active ingredients, and the process of their preparation.

BACKGROUND

Polymorphonuclear leukocytes (leukocytes) provide a principle means of defense against microbial infections. The response to invading microorganisms causes activation of cellular oxidative processes (production of hydroxyl radicals) and nonoxidative processes (digestive enzymes; myeloperoxidase, elastase, etc.) in order to effectively kill microorganisms. However, the response of leukocytes to a foreign challenge can also cause destruction to host tissues and play an important part in the pathogenesis of a number of noninfectious disease conditions.

Leukocytes possess a wide variety of mechanisms that enable them to respond to foreign challenges which are initiated by cell surface receptors. Receptor activation or general cellular activation results in an altered cellular physiology causing the cell in itself to become "activated". The intracellular signaling molecules of activation are often referred to as second messengers, the first messengers being the extracellar activating ligands themselves.

One of the major second messengers in many cells is the calcium ion ($Ca^{+2}$). There are two general ways in which cell-surface receptors are known to generate intracellular calcium signals. One is by activating phospholipase C. Activation of phospholipase C generates inositol trisphosphate which, in turn, releases stored calcium in the cell. Alternatively, cell receptors may open or close gated ion channels, letting calcium enter from outside the cell. $Ca^{+2}$ channels in the plasma membrane are further distinquished to be of two functional types: (1) voltage sensitive calcium channels which are activated when a small and transient flux of ions briefly alter the voltage across the plasma membrane, or (2) receptor operated channels which are directly opened by receptor ligands. The first type of channel operates mainly in voltage sensitive cells such as neurons and muscle cells. Many cells, like leukocytes, are not primarily voltage sensitive cells but have cell-surface receptors that are functionally linked to receptor sensitive $Ca^{+2}$ channels in the plasma membrane. Binding of certain ligands activates these receptors, thereby opening the channels and allowing $Ca^{+2}$ to enter the cytosol, where it then functions as a second messenger.

When cells are activated, corresponding to an influx of $Ca^{+2}$, structures within the cell that bind $Ca^{+2}$ are responsive to such changes, depending on their relative affinity and specificity for calcium. A few $Ca^{+2}$ dependent proteins are known. The first such protein to be discovered and characterized was troponin C found in electrically active skeletal muscle cells. A later discovered calcium binding protein which is ubiquitous in both voltage and receptor sensitive cells is calmodulin.

Among the increasing number of cellular proteins known to be regulated by calmodulin in a $Ca^{+2}$ dependent manner are some forms of cyclic nucleotide phosphodiesterase and adenylate cyclase, as well as membrane bound calcium dependent ATPases, phosphorylase kinase, myosin light chain kinases, and their association with the spindles of the mitotic apparatus and the bundles of actin filaments. Although the total number of proteins that are calcium dependent or are affected by $Ca^{+2}$ dependent enzymes is not known it is clear that calcium is a requirement as a means of activating these processes.

When leukocytes are activated, a number of events can occur which are important in leading to intracellular calcium mediated disease states. For example leukocytes, primarily the neutrophils, are thought to play an integral part in the symptoms and tissue injury of the host in the following diseases; gout, rheumatoid arthritis, immune vasculitis, glomerulonephritis, inflammatory bowel disease, adult respiratory distress syndrome, emphysema, asthma, thermal injury associated with hemolysis, and malignant neoplasms at sites of chronic inflammation (Malech and Gallin; 1987). It therefore appears desirable to inhibit $Ca^{+2}$ uptake in leukocytes in order to alleviate or slow the progression of these immune and inflammatory diseases associated with calcium uptake.

$Ca^{+2}$ uptake in leukocytes and amelioration of immune and inflammatory diseases may also be extended to those diseases associated with the skin and dermal tissues. Included in the list of those topically related inflammatory diseases are those associated with skin and dermis, including neutrophil dermatoses, chronic dermatitis, psoriasis, contact dermatitis, atopic and seborrheic dermatitis, and acne.

Calcium is also an important mediator in thrombocytes (platelets) where it is well known that $Ca^{+2}$ is a required mediator in the intrinsic pathway of blood coagulation. For example, the $Ca^{+2}$ requirement in the blood clotting process and thrombus formation is well known and these processes can be inhibited in vitro, and to some degree in vivo, if chelating agents such as EDTA, citrate, or oxalate are added to bind $Ca^{+2}$. It is recognized that $Ca^{+2}$ plays an integral part of the fibrinolytic cascade and is an active mechanism by which the fibrinolytic response can be modulated therapeutically.

One of the primary functions of platelets occurs at a site of vascular injury wherein they form clot aggregates to close the wound. This response can also have a number of detrimental side effects, for example during ischemic reperfusion the thrombus formation can lead to occlusion of the artery, to the extent of causing a myocardial infarction. It is therefore desirable in many instances to inhibit $Ca^{+2}$ uptake in platelets in order to control the thrombolytic response.

$Ca^{+2}$ entry into the cytosol, by various forms of receptor-mediated activation or by discharge of intracellular stores, is critically linked to certain cellular events of leukocyte activation and platelet aggregation. Altering pathways of $Ca^{+2}$ mobilization provides a mechanism to modulate the responses of leukocytes and platelets. Therefore compounds that inhibit $Ca^{+2}$ mobilization might be expected to reduce $Ca^{+2}$ dependent disease processes associated with leukocyte activation and inhibition in immune and inflammatory diseases and in problems involving platelet aggregation in certain thrombolytic conditions.

SUMMARY OF INVENTION

The present invention relates to novel 1-phenyl-3-aryl-2-propyne-1-one derivatives which are useful as inhibitors of calcium uptake in leukocytes associated with acute and chronic inflammatory and immune diseases, including related disease of the skin and dermal tissues. Finally, this invention relates also to the use of 1-phenyl-3-aryl-2-propyne-1-one derivatives in the treatment of calcium dependent processes of the cardiovascular system including diseases of the thrombolytic system.

This invention relates to compounds of the formula (1):

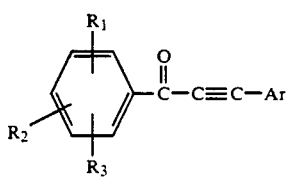
(1)

wherein $R_1$, $R_2$ and $R_3$ are each independently hydrogen; $C_1-C_6$ alkyl; $C_1-C_6$ alkoxy; halogen; $-N(Y_1)(Y_2)$, wherein $Y_1$ and $Y_2$ are each independently hydrogen or $C_1-C_6$ alkyl; or $X_z-(Q)-(CH_2)_n-O-$, wherein Q is phenyl or naphthyl, $n=0$ or 1, $X=C_1-C_6$ alkoxy or $-N(Y_1)(Y_2)$, wherein $Y_1$ and $Y_2$ are as defined previously, and $Z=0, 1, 2$,;

wherein Ar is a radical of the formulae:

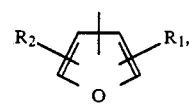
(a)

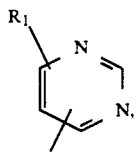
(b)

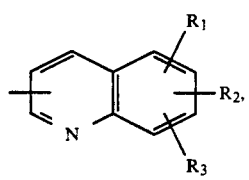
(c)

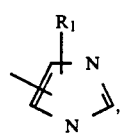
(d)

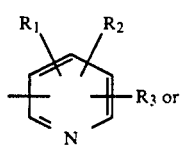
(e) or

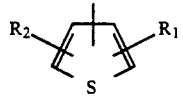
(f)

a pharmaceutically acceptable salt thereof.

The present invention also provides a method of inhibiting calcium uptake in a patient in need thereof comprising administration of a therapeutically effective inhibitory amount of a compound of formula (1).

DETAILED DESCRIPTION OF THE INVENTION

As used herein, the term "$C_1-C_6$ alkyl" refers to a saturated straight or branched chain hydrocarbyl radical of one one to six carbon atoms. Included within the scope of this term are methyl, ethyl, n-propyl, isopropyl, n-butyl, isobutyl, sec-butyl, t-butyl, n-pentyl, n-hexyl, and the like. The term "$C_1-C_6$ alkoxy" refers to methoxy, ethoxy, propoxy and the like. It is also understood that the term $X_z-(Ar)-(CH_2)_n-O-$ specifically includes benzyloxy, (4-methoxy)benzyloxy, (4-dimethylamino)benzyloxy, and the like. The term "halogen" refers to a fluorine, chlorine, bromine, or iodine atom.

The compounds of formula (1) can be prepared by utilizing procedures and techniques well known and appreciated by one of ordinary skill in the art. A general synthetic scheme for preparing compounds of formula (1) is set forth in Scheme A, wherein all substituents, unless otherwise indicated, are previously defined.

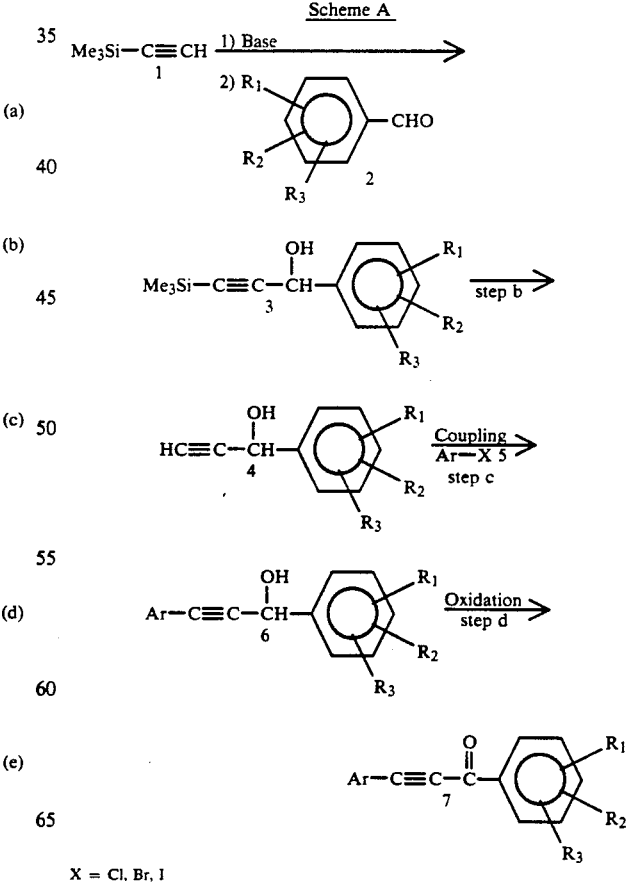

Scheme A

X = Cl, Br, I

In general, a 1-phenyl-3-aryl-2-propyne-1-one compound of structure 7 can be prepared according to Scheme A in a 4-step process.

In step a, trimethylsilylacetylene (1) can first be reacted with a non-nucleophilic base, such as lithium hexamethyldisilazane, in a suitable aprotic solvent, such as tetrahydrofuran. The resulting lithium acetylide can then be reacted with the appropriate benzaldehyde compound of structure 2 to give the corresponding α-[(trimethylsilyl)-ethynyl]-benzenemethanol compound of structure 3.

In step b, the trimethylsilyl functionality of the appropriate α-[(trimethylsilyl)ethynyl]-benzenemethanol compound of structure 3 can be remove by techniques and procedures well known and appreciated by one of ordinary skill in the art. For example, the trimethylsilyl functionality can be removed by reacting the appropriate α-[(trimethylsilyl)ethynyl]-benzenemethanol compound of structure 3 with tetra-n-butylammonium fluoride in a suitable aprotic solvent, such as tetrahydrofuran, to give the corresponding α-(ethynyl)-benzenemethanol compound of structure 4.

In step c, the appropriate α-(ethynyl)-benzenemethanol compound of structure 4 can be coupled with the appropriate aryl halide of structure 5 in the presence of an appropriate coupling catalyst, such as bis(triphenylphosphine)palladium(II) chloride, in a suitable basic solvent, such as diethylamine, along with a catalytic amount of copper(I) iodide to give the corresponding α-[(aryl)ethynyl]-benzenemethanol compound of structure 6.

In step d, the appropriate α-[(aryl)ethynyl]-benzenemethanol compound of structure 6 can be oxidized to the corresponding 1-phenyl-3-aryl-2-propyne-1-one compound of structure 7 by techniques and procedures well known and appreciated by one of ordinary skill in the art. For example, the appropriate α-[(aryl)ethynyl]-benzenemethanol compound of structure 6 can be oxidized to the corresponding 1-phenyl-3-aryl-2-propyne-1-one compound of structure 7 by means of either a Swern oxidation (dimethylsulfoxide, oxalyl chloride and triethylamine), be means of pyridinium dichromate oxidation in a suitable aprotic solvent, such as methylene chloride or by means of barium manganate oxidation in a suitable aprotic solvent, such as methylene chloride Starting materials for use in the general synthetic procedure outlined in Scheme A are readily available to one of ordinary skill in the art.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "mp" refers to melting point; "mg" refers to milligrams; "μM" refers to micromolar; "μg" refers to micrograms.

EXAMPLE 1

1-(4-Dimethylaminophenyl)-3-(4-pyridinyl)-2-propyne-1-one

Step a:
4-Dimethylamino-α-[(trimethylsilyl)ethynyl]-benzenemethanol

Place lithium hexamethyldisilazane (12 mL of a 1 M solution in tetrahydrofuran, 12 mmol) under an argon atmosphere and cool to 0° C. Add trimethylsilylacetylene (1.7 mL, 12 mmol) and stir for 1 hour at 0° C. Add 4-dimethylaminobenzaldehyde (1.49 g, 10 mmol) in tetrahydrofuran (25 mL). Allow to warm to room temperature and stir for 3 hours. Pour the mixture into ethyl ether and water, separate the organic phase and evaporate the solvent in vacuo. Filter the oil through silica gel (20% ethyl acetate/hexane) and evaporate the solvent in vacuo to yield 2.26 g of the title compound.

Step b: 4-Dimethylamino-α-(ethynyl)-benzenemethanol

Place a mixture of 4-dimethylamino-α-[(trimethylsilyl)-ethynyl]-benzenemethanol (2.26 g, 9.13 mmol) and tetrahydrofuran (11 mL) under argon atmosphere. Add, by dropwise addition, tetra-n-butylammonium fluoride (11 mL of a 1 M solution in tetrahydrofuran, 11 mmol). Stir for 1 hour at room temperature and partition between ethyl ether and water. Separate the organic phase, wash with saturated aqueous sodium chloride, dry (MgSO4), filter, and concentrate in vacuo to yield 1.37 g, (85.6%) of the title compound.

Step c:
4-Dimethylamino-α-[(4-pyridinyl)ethynyl]-benzenemethanol

Place 4-bromopyridine hydrochloride (0.78 g, 4 mmol), 4-dimethylamino-α-(ethynyl)-benzenemethanol (0.88 g, 5 mmol) and diethylamine (25 mL) under nitrogen atmosphere. Add bis(triphenylphosphine)palladium(II) chloride (140 mg) then copper(I) iodide (20 mg). Stir overnight at room temperature and filter. Evaporate the solvent in vacuo and filter through silica gel (2:1 ethyl acetate/hexane). Evaporate the solvent in vacuo and recrystallize (25% ethyl acetate/hexane) to yield 0.5 g of the title compound; mp 117° C.

Step d:
1-(4-Dimethylaminophenyl)-3-(4-pyridinyl)-2-propyne-1-one

Place pyridinium dichromate (1.75 g) and methylene chloride (20 mL) under argon atmosphere and cool to 0° C. Add a 1:1 mixture of 4-dimethylamino-α-[(4-pyridinyl)ethynyl]-benzenemethanol and 4-dimethylamino-α-(ethynyl)-benzenemethanol (0.8 g). Stir overnight while slowly warming to room temperature. Dilute with ethyl ether and filter the chromium salts. Purify by silica gel chromatography (2:1 ethyl acetate/hexane) to yield 0.94 g of the title compound; mp 143°–145° C.

EXAMPLE 2

1-Phenyl-3-(4-pyridinyl)-2-propyne-1-one

Step a: α-[(Trimethylsilyl)ethynyl]-benzenemethanol

Place lithium hexamethyldisilazane (20 mL of a 1 M solution in tetrahydrofuran, 20 mmol) under an argon atmosphere and cool to 0° C. Add, by dropwise addition, trimethylsilylacetylene (2.83 mL, 20 mmol) and stir for 1 hour at 0° C. Add benzaldehyde (2.03 mL, 20 mmol) in tetrahydrofuran (10 mL). Allow to warm to room temperature and stir for 1 hour. Pour the mixture into ethyl ether and water, separate the organic phase and evaporate the solvent in vacuo. Filter the oil through silica gel (20% ethyl acetate/hexane) and evaporate the solvent in vacuo to yield 4.09 g of the title compound.

Step b: α-(Ethynyl)-benzenemethanol

Place a mixture of α-[(trimethylsilyl)ethynyl]-benzene-methanol (4.09 g, 20 mmol) and tetrahydrofuran (25 mL) under argon atmosphere and cool to 0° C. Add, by dropwise addition, tetra-n-butylammonium fluoride (25 mL of a 1M solution in tetrahydrofuran, 25 mmol). Allow to warm to room temperature and stir for 1 hour. Partition between ethyl ether and water. Separate the organic phase, wash with saturated aqueous sodium chloride and concentrate in vacuo. Purify by silica gel chromatography (15% ethyl acetate/hexane) then purify further by distillation to yield 2.15 g of the title compound; bp 100°-110° C. @0.1 mm Hg.

Step c: α-[(4-Pyridinyl)ethynyl]-benzenemethanol

Place 4-bromopyridine hydrochloride (2.33 g, 12 mmol), α-(ethynyl)-benzenemethanol (1.95 g, 14.8 mmol) and diethylamine (25 mL) under nitrogen atmosphere. Add bis(triphenylphosphine)palladium(II) chloride (105 mg) then copper(I) iodide (59 mg). Stir at room temperature for 3 hours. Evaporate the solvent in vacuo, stir the residue in ethyl acetate (50 mL) and filter the solids. Evaporate the solvent in vacuo and purify by silica gel chromatography (4:3 ethyl acetate/hexane) to yield 0.4 g. Recrystallize (hexane/chloroform) to yield 0.2 g of the title compound; mp 93°-96° C.

Step d: 1-Phenyl-3-(4-pyridinyl)-2-propyne-1-one

Place oxalyl chloride (0.5 mL of a 2 M solution in methylene chloride, 1 mmol) under argon atmosphere and cool with a dry ice/acetone bath. Add dimethylsulfoxide (0.14 mL, 2 mmol) and stir for 10 minutes at −70° C. Add α-[(4-pyridinyl)ethynyl]-benzenemethanol (0.18 g, 0.86 mmol) in methylene chloride (1 mL). Stir for 20 minutes at −78° C. Add triethylamine (0.56 mL, 4 mmol), remove the cooling bath and stir for 45 minutes. Pour onto silica gel and elute with 60% ethyl acetate/hexane. Evaporate the solvent in vacuo and recrystallize (hexane/chloroform) to yield 58.1 mg of the title compound; mp 74°-75° C.

EXAMPLE 3

1-Phenyl-3-(3-pyridinyl)-2-propyne-1-one

Step a: α-[(Trimethylsilyl)ethynyl]-benzenemethanol

Place lithium hexamethyldisilazane (12 mL of a 1M solution in tetrahydrofuran, 12 mmol) under an argon atmosphere and cool to 0° C. Add trimethylsilylacetylene (1.7 mL, 12 mmol) and stir for 1 hour at 0° C. Add benzaldehyde (1.06 g, 10 mmol) in tetrahydrofuran (25 mL). Allow to warm to room temperature and stir for 3 hours. Pour the mixture into ethyl ether and water, separate the organic phase and evaporate the solvent in vacuo. Filter the oil through silica gel (20% ethyl acetate/hexane) and evaporate the solvent in vacuo to yield the title compound.

Step b: α-(Ethynyl)-benzenemethanol

Place a mixture of α-[(trimethylsilyl)ethynyl]-benzene-methanol (1.87 g, 9.13mmol) and tetrahydrofuran (11 mL) under argon atmosphere. Add, by dropwise addition, tetra-n-butylammonium fluoride (11 mL of a 1M solution in tetrahydrofuran, 11 mmol). Stir for 1 hour at room temperature and partition between ethyl ether and water. Separate the organic phase, wash with saturated aqueous sodium chloride, dry (MgSO₄), filter, and concentrate in vacuo to yield the title compound.

Step c: α-[(3-Pyridinyl)ethynyl]-benzenemethanol

Place 3-bromopyridine hydrochloride (0.78 g, 4 mmol), α-(ethynyl)-benzenemethanol (661 mg, 5 mmol) and diethylamine (25mL) under nitrogen atmosphere. Add bis(triphenyl-phosphine)palladium(II) chloride (140mg) then copper(I) iodide (20 mg). Stir overnight at room temperature and filter. Evaporate the solvent in vacuo and filter through silica gel (2:1 ethyl acetate/hexane). Evaporate the solvent in vacuo and recrystallize (25% ethyl acetate/hexane) to yield the title compound.

Step d: 1-Phenyl-3-(3-pyridinyl)-2-propyne-1-one

Place pyridinium dichromate (1.75 g) and methylene chloride (20 mL) under argon atmosphere and cool to 0° C. Add α-[(3-pyridinyl)ethynyl]-benzenemethanol (663 mg, 3.2 mmol)). Stir overnight while slowly warming to room temperature. Dilute with ethyl ether and filter the chromium salts. Purify by silica gel chromatography (2:1 ethyl acetate/hexane) to yield the title compound.

EXAMPLE 4

1-(4-Diethylaminophenyl)-3-(4-pyridinyl)-2-propyne-1-one

Step a:
α-(Trimethylsilyl)ethynyl]-(4-diethylamino)-benzenemethanol

Place lithium hexamethyldisilazane (12 mL of a 1M solution in tetrahydrofuran, 12 mmol) and tetrahydrofuran (40 mL) under an argon atmosphere and cool to 0° C. Add trimethylsilyl-acetylene (1.69 mL, 12 mmol) and stir for 45 minutes at 0° C. Add a solution of 4-diethylaminobenzaldehyde (1.77 g, 10 mmol) in tetrahydrofuran (10 mL). Remove the cooling bath and stir at room temperature for 1 hour. Pour onto ethyl ether and water, separate the organic phase and dry (MgSO4). Filter and evaporate the solvent in vacuo to yield 2.8 g of the title compound.

Step b: α-[Ethynyl]-(4-diethylamino)benzenemethanol

Place α-[ethynyl]-(4-diethylamino)-benzenemethanol (2.8 g) in tetrahydrofuran (15 mL) under an argon atmosphere and cool to 0° C. Add a solution of 1M tetra-n-butylammonium fluoride in tetrahydrofuran (15mL, 15mmol). Remove the cooling bath and stir at room temperature for 2 hours. Pour onto ethyl ether and water, separate the organic phase, then wash with saturated aqueous sodium chloride. Evaporate the solvent in vacuo to yield a dark oil. Pour onto silica gel and elute with 20% ethyl acetate/hexane to yield 1.67 g of the title compound.

Step c:
α-[(4-Pyridinyl)ethynyl]-(4-diethylamino)-benzenemethanol

Place 4-bromopyridine hydrochloride (1.40 g, 7.2 mmol), α-[ethynyl]-(4-diethylamino)benzenemethanol (1.67 g, 8.2 mmol) and diethylamine (35 mL) under an argon atmosphere. Add bis(triphenylphophine)palladium chloride (II) (0.2 g) and copper (I) iodide (70 mg) and stir at room temperature overnight. Filter the solids off, evaporate the diethyl-amine in vacuo, and purify by silica gel chromatography (60% ethyl acetate/hexane) to yield 1.4 g of the title compound; mp 100°–103° C.

Step d:
1-(4-Diethylaminophenyl)-3-(4-pyridinyl)-2-propyne-1-one

Mix α-[(4-pyridinyl)ethynyl]-(4-diethylamino)-benzene-methanol (1.4 g) and pyridinium dichromate (2.82 g) and methylene chloride (25 mL). Stir overnight at room temperature. Dilute with 4 times the volume of ethyl ether. Filter the solid chromium salts off and evaporate the solvent in vacuo. Crystallize the residue with 20% ethyl ether/hexane. Filter the bright yellow solid and air dry to yield 0.16 g (1st crop) and 0.23 g (2nd crop) of the title compound; mp 85°–7° C.

EXAMPLE 5

1-(4-Dimethylaminophenyl)-3-(4-pyrimidinyl)-2-propyne-1-one

Step c:
α-[(4-Pyrimidinyl)ethynyl]-(4-diethylamino)-benzenemethanol

Place 4-bromopyrimidine (1.75 g, 11 mmol), α-[ethynyl]-(4-diethylamino)benzenemethanol (Example 1, Step b) (2.45 g, 14 mmol) and diethylamine (75 mL) under an argon atmosphere. Add bis(triphenylphophine)palladium chloride (II) (240 mg) and copper (I) iodide (40 mg) and stir at room temperature for three hours. Filter the solids off, evaporate the diethylamine in vacuo, and purify by silica gel chromatography (60% ethyl acetate/hexane) to yield 0.79 g of the title compound; mp 131°–134° C.

Step d:
1-(4-Diethylaminophenyl)-3-(4-pyrimidinyl)-2-propyne-1-one

Mix α-[(4-pyrimidinyl)ethynyl]-(4-diethylamino)-benzenemethanol (0.7 g) and barium manganate (1 g) and methylene chloride (25 mL). Stir overnight at room temperature. Pour onto silica gel and elute with 60% ethyl acetate/hexane amd recrystallize (chloroform/hexane) to yield 0.35 g of the title compound; mp 180°–2° C.

EXAMPLE 6

1-(4-Diethylaminophenyl)-3-(4-quinolinyl)-2-propyne-1-one Step c:
α-[((4-Quinolinyl)ethynyl]-4-diethylamino)-benzenemethanol Place 4-bromoquinoline (2.08 g, 10 mmol), α-[ethynyl]-(4-diethylamino)benzenemethanol (Example 1, Step b) (2.10 g, 12 mmol) and diethylamine (50 mL) under an argon atmosphere. Add bis(triphenylphophine)palladium chloride (II) (230 mg) and copper (I) iodide (35 mg) and stir at room temperature for three hours. Filter the solids off, evaporate the diethylamine in vacuo, and purify by silica gel chromatography (60% ethyl acetate/hexane) and recrystallize (20% ethyl ether/hexane) to yield 1.9 g of the title compound; mp 115°–117° C.

Step d:
1-(4-Diethylaminophenyl)-3-(4-quinolinyl)-2-propyne-1-one

Mix α-[(4-quinolinyl)ethynyl]-(4-diethylamino)-benzene-methanol (1.81 g, 6 mmol) and methylene chloride (100 mL) and cool in an ice-water bath. Add barium manganate (2.31 g, 9 mmol) and remove the cooling bath. Stir for 16 hours at room temperature. Pour onto silica gel and elute with 60% ethyl acetate/hexane and recrystallize (chloroform/hexane) to yield 0.51 g of the title compound; mp 163°–5° C.

Alternatively, compounds of formula (1) can be prepared according to the procedure set forth in Scheme B, wherein all substituents, unless otherwise indicated, are previously described.

Scheme B

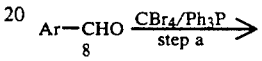

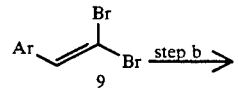

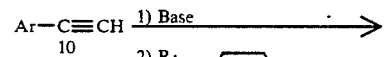

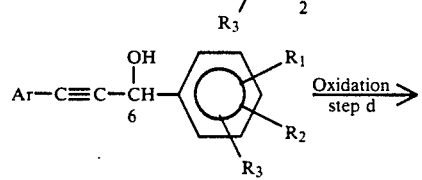

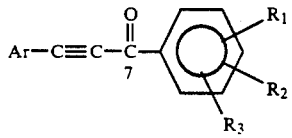

In general, a 1-phenyl-3-aryl-2-propyne-1-one compound of structure 7 can be prepared in a 4-step process.

In step a, the appropriate 2',2'-dibromostyrene compound of structure 9 can be prepared by reacting the appropriate aryl aldehyde compound of structure 8 with carbon tetrabromide and triphenylphosphine in a suitable aprotic solvent, such as methylene chloride.

In step b, the appropriate arylacetylene compound of structure 10 can be prepared by reacting the appropriate 2',2'-dibromostyrene compound of structure 9 with a non-nucleophilic base, such as n-butyllithium in a suitable aprotic solvent, such as tetrhydrofuran.

In step c, the appropriate α-[(aryl)ethynyl]-benzenemethanol compound of structure 6 can be prepared by first reacting the appropriate arylacetylene compound of structure 10 with a non-nucleophilic base, such as lithium hexamethyldisilazane. The corresponding lithium acetylide can then be reacted with the appropriate benzaldehyde compound of structure 2 to give the appropriate α-[(aryl)ethynyl]-benzenemethanol compound of structure 6.

In step d, the appropriate α-[(aryl)ethynyl]-benzenemethanol compound of structure 6 can be oxidized to the corresponding 1-phenyl-3-aryl-2-propyne-1-one compound of structure 7 by techniques and procedures well known and appreciated in the art and described previously in Scheme A.

Starting materials for use in the general synthetic procedure outlined in Scheme A are readily available to one of ordinary skill in the art.

The following examples present typical syntheses as described in Scheme A. These examples are understood to be illustrative only and are not intended to limit the scope of the present invention in any way.

EXAMPLE 7

1-Phenyl-3-(2-imidazolyl)-2-propyne-1-one

Step a: 2-(2',2'-Dibromoethenyl)-imidazole

Mix carbon tetrabromide (49.8 g, 150 mmol) and methylene chloride (75 mL) and cool to 0° C. Add, by dropwise addition, a solution of triphenylphosphine (78.6 g, 300 mmol) in methylene chloride (75 mL). Stir at 0° C. for 30 minutes. Add, by dropwise addition, a solution of 2-imidazole-carboxaldehyde (7.57 g, 78.8 mmol) in methylene chloride (75 mL). Remove the cooling bath and stir at room temperature until the reaction is complete. Pour onto ethyl ether and water, separate the organic layer and dry ($MgSO_4$). Filter and evaporate the solvent in vacuo. Purify by silica gel chromatography to yield the title compound.

Step b: 2-Imidazolylacetylene

Place 2-(2',2'-dibromoethenyl)imidazole (5.6 g, 22.3 mmol) and tetrahydrofuran (70 mL) under argon atmosphere and cool to −78° C. Add, by dropwise addition, n-butyllithium (18.7 mL of a 2.5M solution in hexane, 46.8 mmol). Stir for 1 hour at -78° C., remove the cooling bath and stir at room temperature until the reaction is complete. Pour onto ethyl ether and water, separate the organic layer and dry ($MgSO_4$). Filter and evaporate the solvent in vacuo. Purify by silica gel chromatography to yield the title compound.

Step c: α-[(2-Imidazolyl)ethynyl]-benzenemethanol

Place lithium hexamethyldisilazane (3 mL of a 1M solution in tetrahydrofuran, 3 mmol) under argon atmosphere and cool to 0° C.. Add 2-imidazolylacetylene (276 mg, 3 mmol) in tetrahydrofuran (20 mL) and stir at 0° C. until anion formation is complete. Add a solution of benzaldehyde (297 mg, 2.8 mmol) in tetrahydrofuran, remove the ice bath and stir at room temperature until the reaction is complete. Pour onto ethyl ether and water, separate the organic layer and dry ($MgSO_4$). Filter and evaporate the solvent in vacuo. Purify by silica gel chromatography to yield the title compound.

Step d: 1-Phenyl-3-(2-imidazolyl)-2-propyne-1-one

Place pyridinium dichromate (0.75 g, 2 mmol) and methylene chloride (15 mL) under argon atmosphere and cool to 0° C. Add α-[(2-imidazolyl)ethynyl]-benzenemethanol (297 mg, 1.5 mmol). Stir overnight while slowly warming to room temperature. Dilute with ethyl ether and filter the chromium salts. Purify by silica gel chromatography to give the title compound.

EXAMPLE 8

1-Phenyl-3-(thiophen-2-yl)-2-propyne-1-one

Step a: 2-(2',2'-Dibromoethenyl)-thiophene

Mix carbon tetrabromide (49.8 g, 150 mmol) and methylene chloride (75 mL) and cool to 0° C. Add, by dropwise addition, a solution of triphenylphosphine (78.6 g, 300 mmol) in methylene chloride (75 mL). Stir at 0° C. for 30 minutes. Add, by dropwise addition, a solution of 2-thiophene-carboxaldehyde (8.75 g, 78.8 mmol) in methylene chloride (75 mL). Remove the cooling bath and stir at room temperature until the reaction is complete. Pour onto ethyl ether and water, separate the organic layer and dry ($MgSO_4$). Filter and evaporate the solvent in vacuo. Purify by silica gel chromatography to yield the title compound.

Step b: (Thiophen-2-yl)acetylene

Place 2-(2',2'-dibromoethenyl)thiophene (5.97 g, 22.3 mmol) and tetrahydrofuran (70 mL) under argon atmosphere and cool to −78° C. Add, by dropwise addition, n-butyllithium (18.7 mL of a 2.5 M solution in hexane, 46.8 mmol). Stir for 1 hour at −78° C., remove the cooling bath and stir at room temperature until the reaction is complete. Pour onto ethyl ether and water, separate the organic layer and dry ($MgSO_4$). Filter and evaporate the solvent in vacuo. Purify by silica gel chromatography to yield the title compound.

Step c: α-[(Thiophen-2-yl)ethynyl]-benzenemethanol

Place lithium hexamethyldisilazane (3 mL of a 1M solution in tetrahydrofuran, 3 mmol) under argon atmosphere and cool to 0° C. Add (thiophen-2-yl)acetylene (324 mg, 3 mmol) in tetrahydrofuran (20 mL) and stir at 0° C. until anion formation is complete. Add a solution of benzaldehyde (297 mg, 2.8 mmol) in tetrahydrofuran, remove the ice bath and stir at room temperature until the reaction is complete. Pour onto ethyl ether and water, separate the organic layer and dry ($MgSO_4$). Filter and evaporate the solvent in vacuo. Purify by silica gel chromatography to yield the title compound.

Step d: 1-Phenyl-3-(thiophen-2-yl)-2-propyne-1-one

Place pyridinium dichromate (0.75 g, 2 mmol) and methylene chloride (15 mL) under argon atmosphere and cool to 0° C. Add α-[(2-thiophenyl)ethynyl]-benzenemethanol (321 mg, 1.5 mmol). Stir overnight while slowly warming to room temperature. Dilute with ethyl ether and filter the chromium salts. Purify by silica gel chromatography to give the title compound.

EXAMPLE 9

1-Phenyl-3-(2-furanyl)-2-propyne-1-one

Step a: 2-(2',2'-Dibromoethenyl)furan

Mix carbon tetrabromide (49.8 g, 150 mmol) and methylene chloride (75 mL) and cool to 0° C. Add, by dropwise addition, a solution of triphenylphosphine (78.6 g, 300 mmol) in methylene chloride (75 mL). Stir at 0° C. for 30 minutes. Add, by dropwise addition, a solution of 2-furan-carboxaldehyde (7.57 g, 78.8 mmol) in methylene chloride (75 mL). Remove the cooling bath and stir at room temperature until the reaction is complete. Pour onto ethyl ether and water, separate the organic layer and dry ($MgSO_4$). Filter and evaporate the solvent in vacuo. Purify by silica gel chromatography to yield the title compound.

Step b: 2-Furanylacetylene

Place 2-(2',2'-dibromoethenyl)furan (5.6 g, 22.3 mmol) and tetrahydrofuran (70 mL) under argon atmosphere and cool to -78° C. Add, by dropwise addition, n-butyllithium (18.7 mL of a 2.5M solution in hexane, 46.8 mmol). Stir for 1 hour at −78° C., remove the cooling bath and stir at room temperature until the reaction is complete. Pour onto ethyl ether and water, separate the organic layer and dry (MgSO$_4$). Filter and evaporate the solvent in vacuo. Purify by silica gel chromatography to yield the title compound.

Step c: α-[(2-Furanyl)-ethynyl]-benzenemethanol

Place lithium hexamethyldisilazane (3 mL of a 1M solution in tetrahydrofuran, 3 mmol) under argon atmosphere and cool to 0° C. Add 2-furanylacetylene (276 mg, 3 mmol) in tetrahydrofuran (20 mL) and stir at 0° C. until anion formation is complete. Add a solution of benzaldehyde (297 mg, 2.8 mmol) in tetrahydrofuran, remove the ice bath and stir at room temperature until the reaction is complete. Pour onto ethyl ether and water, separate the organic layer and dry (MgSO$_4$). Filter and evaporate the solvent in vacuo. Purify by silica gel chromatography to yield the title compound.

Step d: 1-Phenyl-3-(2-furanyl)-2-propyne-1-one

Place pyridinium dichromate (0.75 g, 2 mmol) and methylene chloride (15 mL) under argon atmosphere and cool to 0° C. Add α-[(2-furanyl)ethynyl]-benzenemethanol (297 mg, 1.5 mmol). Stir overnight while slowly warming to room temperature. Dilute with ethyl ether and filter the chromium salts. Purify by silica gel chromatography to give the title compound.

The following compounds can be prepared by procedures analogous to those described above in Examples 1–9:

1-phenyl-3-(2-pyridinyl)-2-propyne-1-one;
1-phenyl-3-(1-imidazolyl)-2-propyne-1-one;
1-phenyl-3-(3-imidazolyl)-2-propyne-1-one;
1-phenyl-3-(thiophen-3-yl)-2-propyne-1-one;
1-phenyl-3-(2-furanyl)-2-propyne-1-one;
1-(4-dimethylaminophenyl)-3-(2-pyridinyl)-2-propyne-1-one;
1-(4-dimethylaminophenyl)-3-(3-pyridinyl)-2-propyne-1-one;
1-(4-dimethylaminophenyl)-3-(3-imidazolyl)-2-propyne-1-one;
1-(4-dimethylaminophenyl)-3-(2-imidazolyl)-2-propyne-1-one;
1-(4-dimethylaminophenyl)-3-(1-imidazolyl)-2-propyne-1-one;
1-(4-dimethylaminophenyl)-3-(2-thiophenyl)-2-propyne-1-one;
1-(4-dimethylaminophenyl)-3-(thiophen-3-yl)-2-propyne-1-one;
1-(4-dimethylaminophenyl)-3-(2-furanyl)-2-propyne-1-one;
1-(4-dimethylaminophenyl)-3-(3-furanyl)-2-propyne-1-one;
1-(4-dimethylaminophenyl)-3-(2-pyrimidinyl)-2-propyne-1-one;
1-(4-dimethylaminophenyl)-3-(3-pyrimidinyl)-2-propyne-1-one;
1-(4-dimethylaminophenyl)-3-(2-quinolinyl)-2-propyne-1-one;
1-(4-dimethylaminophenyl)-3-(3-quinolinyl)-2-propyne-1-one.

One embodiment of the present invention provides a method of inhibiting of calcium uptake in leukocytes. As used herein the term "inhibition" refers to any process whereby the uptake of calcium into leukocytes is slowed, interrupted, arrested, or stopped and does not necessarily indicate a total elimination of calcium uptake into the affected cells or tissues.

The terms calcium and calcium ion (Ca$^{+2}$) may be used interchangably herein to refer to the element of calcium and its ion states which ever maybe actively involved the cellular processes of leukocytes. Furthermore, it is understood that inhibition of calcium uptake into leukocytes by compounds of formula (1) may affect one or more of elemental states of calcium and should not be limited to any ionic form of calcium and/or its association with any particular counterion; for example, calcium chloride, calcium carbonate, calcium flouride, etc. are all known and would be considered within the definition of calcium used herein.

Calcium uptake into leukocytes is one of the signatory events of leukocyte activation and serves as a second messenger to the cell. Often the uptake of calcium is dependent on some first messenger, as for example, the binding of a ligand to its cell surface receptor. Binding of the ligands to their receptors can serve to open Ca$^{+2}$ channels, allowing Ca$^{+2}$ to enter the cytosol, where it then functions as a second messenger. When cells are activated, corresponding to an influx of Ca$^{+2}$ a number of events can occur which lead or contibute to immunological or inflammatory based diseases.

Leukocytes encompass a class of cells of the immune system that are histologically and biochemically distinct from other cells of the immune system. Leukocytes as referred to herein encompass five major classes of cells: neutrophils, basophils, eosinophils, macrophages, and lymphocytes. Within these cell classes can be further classifications of cell types; for example, neutrophils can be further understood to include polymorphonuclear leukocytes. All major classes of leukocytes are related in that they are derived from a progenitor myeloid stem cell. Although the term neutrophil is used extensively herein, it is used to be exemplary of the action of leukocytes as all cells derived from myeloid stem cells and is not meant as any limitation upon the use or administration of compounds of the formula (1) that may be causative or symptomatic from the action of any particular type of leukocytes or cell of the immune system. Furthermore, the action of a leukocytes, wherein the process is to limit or stop the uptake of calcium to affect a cure in a disease process is not limited by the disease being effected by multiple cell or tissue types and encompasses a complex interaction of cellular and tissue interactions. One embodiment of the invention is the inhibition of calcium uptake in leukocytes wherein the effect of inhibition results in a beneficial modulation of phagocytic functions of leukocytes. It is therefore further understood that leukocytic cells can be classified by the functionality inhibited; for example, one could use the term phagocytes or cells with phagocytic functions as a group or subgroup of cells encompassing the cells known as leukocytes herein.

Leukocytes respond to a large variety of inflammatory and immune conditions. During these events receptor activation or general cellular activation results in an altered cellular physiology wherein the leukocyte becomes activated. Often the term "activation" is used to refer to the process or state of leukocytes that have become activated that can be characterized by the cells response to take up calcium while becoming activated or maintaining the state of activation.

The activation of cellular oxidative and nonoxidative mechanisms that result from leukocyte activation play an important role in the development of a number of immune diseases processes. As part of the cellular defense system, including the adverse symptoms and tissue injury of the host, activation of participating leukocytes is in part calcium dependent. The noninfectious disease processes in which leukocytes, primarily the neutrophils, are thought to play an integral part in the symptoms and tissue injury of the host include; gout, rheumatoid arthritis, immune vasculitis, glomerulonephritis, neutrophil dermatoses, inflammatory bowel disease, myocardial infarction, adult respiratory distress syndrome, emphysema, asthma, thermal injury associated with hemolysis, and malignant neoplasms at sites of chronic inflammation (Malech and Gallin; 1987).

In a number of autoimmune diseases, such as gout, autoimmune arthritides, autoimmune vasculitis and some forms of glomerulonephritis, neutrophils are found to accumulate in the areas of the joint and serve to contribute to the destruction of joint and soft tissue. Although a number of disease processes are involved in the patho-physiology of these diseases the recruitment of neutrophils into the area is well documented and may be responsible to a large part of the observable histopathological aspects of these diseases. Therein, a number of studies in model systems have clearly demonstrated that nonoxidative processes which would result from neutrophil activation, particularly the release of neutrophil elastase and other proteolytic and glycolytic enzymes, can directly damage host tissues.

A large variety of dermatopathic disorders are associated with the infiltration of neutrophils into the ectodermal and dermal tissues of the skin. Included with the diseases of the skin wherein neutrophils participate in the progression of the disease, but not limited to, are forms of psoriasiform dermatoses, vessel-based neutrophilic dermatoses as found in Sweet's syndrome and Behcet's disease, and pyoderma gangrenosum. In these disease processes neutrophils serve to augment and maintain the inflammmatory symptoms, enhance tissue injury, and may thereby prevent healing.

A number of other diseases, such as inflammatory bowel disease and myocardial infarction, are related to defective neutrophil function within a particular organ. Studies in animals suggest that abnormalities in the circulation of the neutrophils in the bowel result in an abnormal activation of these cells. In the same sense, neutrophils have been shown to be recruited to the infarction in the myocardial tissues and to play a part in enhancing tissue injury after a myocardial infarction.

The pathogenesis of a number of respiratory disorders including adult respiratory distress syndrome (ARDS), emphysema, and asthma have been associated with neutrophil infiltration and aggravation of the disease. Neutrophil mediated oxidative damage of the pulmonary tissues may be an important component of the pathogenesis of the these respiratory disorders. Further, neutrophil accumulation with the release of elastase may have an important role in the tissue destruction occurring in emphysema and may have an important role in the late phases of the inflammatory response in allergic asthma. The allergic response, during which neutrophils release their constituents, may occur from the release of histamine by mast cells.

Neutrophil activation may serve in the general pathogenesis of diseases related to complement activation. It is well known that complement can serve to activate neutrophils with the concomitant production of hydroxyl radicals. The production of hydroxyl radicals from neutrophil activation may therein be responsible for erythrocyte fragility and intravascular hemolysis associated with complement activation.

The term "inflammation" as used herein is considered as a process that most often involves leukocytes of the immune system and is the process involved in a "inflammatory condition". Clinically, the cardinal signs of inflammation may include one or more of the following symptoms: redness, swelling, heat, pain, loss of function, and fever. However certain cellular events accompanying inflammation include, but not limited to, leukocyte activation, leukocyte margination and emigration, and leukocyte exudation. It is also considered that any condition in which there exist an early or latent inflammatory state, leukocytes may participate in its underlying causes or serve to perpetuate or expand the disease state or condition. Therein, processes involving an inflammatory condition are considered herein to involve leukocytes of the immune system and as such can be viewed within the repertoire of "immune diseases" and conditions affected by leukocytes capable of being treated with compounds of the formula (1). It is also considered that compounds of the present invention that affect the uptake of calcium into leukocytes are thought to be potentially beneficial in the amelioration of conditions involving inflammation and/or immune diseases.

The development of methods like those of the present invention to abrogate neutrophil responses or to inactivate neutrophil oxidative metabolites and granule contents will be useful in limiting tissue destruction in these noninfectious inflammatory diseases.

Platelets (thrombocytes) are non-nucleated cells of the blood that are derived from megakaryocytes of the the bone marrow. Platelets are also required for the clotting of blood and help repair breaches in the walls of blood vessels. The platelet response to form clots and to repair damaged vascular tissue can also have a number of detrimental side effects; for example, during ischemic reperfusion the thrombus formation and associated platelet aggregation can lead eventually to occlusion of the artery. It is also well known in the field that the closing or occlusion of the walls of the arteries and veins can lead to the occurrence of a myocardial infarction. It is also well known that calcium is required in the blood clotting process and for thrombus formation; for example modulation of the clotting response by EDTA and other chelators that bind calcium is firmly established in the field. It is thereby envisioned that inhibiting calcium uptake into platelets may render itself as a viable means by which to modulate platelet activation therapeutically, which would include the release of vasoactive mediators and formation of platelet aggregates, where such use is administered to a patient in need thereof. As used herein, the term "patient" refers to a warm blooded animal such as a mammal which is afflicted with a particular immune disease state. It is understood that dogs, cats, rats, mice, horses, cattle, sheep, and humans are examples of animals within the scope of the meaning of the term.

The compounds of formula (1) are believed to exert their inhibitory effect on calcium uptake in leukocytes and platelets and thereby provide relief of calcium dependent mechanisms involved in immunoregulation, including inflammatory and immune diseases. However, it is understood that the present invention is not limited by any particular theory or proposed mechanism to explain its effectiveness in and end-use application. It is also understood that the use of the term compounds of the formula (1) is also inclusive of all its radicals that include derivatives (1a), (1b), (1c), and (1d).

As is well known and appreciated by those skilled in the art, various disease states in certain inflammatory and immune diseases are characterized by an events that lead calcium uptake into leukocytes. As used herein, events that lead to calcium uptake in leukocytes can either refer to the initial events leading to the initial condition or events associated with maintaining an inflammatory or immune condition. Furthermore, it is also well known and appreciated by those skilled in the art that certain cardiovascular diseases are characterized by events leading to calcium uptake in platelets and such events may thereto refer either to the initial events leading to the condition or to events associated with maintaining the cardiovascular disease state.

More specifically, the present invention provides a method for the treatment of a patient afflicted with a calcium dependent disease state in leukocytes, wherein such disease states may be, but not limited to, an inflammatory or immune disease, that comprises the administration of a effective calcium uptake inhibitory amount of a compound of formula (1).

A therapeutically effective calcium uptake inhibitory amount of a compound of formula (1) refers to an amount which is effective in controlling the activation of leukocytes involved in a immune disease state. The term "controlling the activation" is intended to refer to all processes wherein there may be a slowing, interrupting, arresting, or stopping of the progression of the immune disease and does not necessarily indicate a total elimination of all disease symptoms.

Furthermore, it is also well known and appreciated by those skilled in the art that certain cardiovascular diseases are characterized by events leading to calcium uptake in platelets and such events may thereto refer either to the initial events leading to the condition or to events associated with maintaining the cardiovascular disease state.

The present invention also provides a method for the treatment of a patient afflicted with a calcium dependent disease state in platelets, wherein such disease states may be, but not limited to, cardiovascular diseases, that comprises the administration of a effective calcium uptake inhibitory amount of a compound of formula (1).

A therapeutically effective calcium uptake inhibitory amount of a compound of formula (1) refers to an amount which is effective in controlling the platelet function involved in a cardiovascular disease state. The term controlling the platelet function involved in a cardiovascular disease refers to slowing, interrupting, arresting, or stopping the progression of the cardiovascular disease and does not necessarily indicate a total elimination of all disease symptoms.

A therapeutically effective inhibitory amount in either a immune or cardiovascular condition or disease, can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (1) is expected to vary from about 0.1 milligram per kilogram of body weight per day (nag/kg/day) to about 100 mg/kg/day. Preferred amounts are expected to vary from about 0.5 to about 10 mg/kg/day.

In effecting treatment of a patient afflicted with a disease state described above, a compound of formula (1) can be administered in any form or mode which makes the compound bioavailable in effective amounts, including oral and parenteral routes. For example, compounds of formula can be administered orally, subcutaneously, intramuscularly, intravenously, transdermally, intranasally, rectally, topically, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides pharmaceutical compositions comprising a effective amount of a compound of formula (1) in admixture or otherwise in association with one or more pharmaceutically acceptable carriers or excipients. The term "effective calcium uptake inhibitory amount" as applied to compounds of formula (1) refers to effective inhibitory amounts as appropriate to inhibit the uptake of calcium in leukocytes wherein such inhibition may be for a patient suffering from an immune or inflammatory disease. Further the term "effective calcium uptake inhibitory amount" as applied to compounds of (1) also refers to effective inhibitory amounts as appropriate to inhibit the uptake of calcium in platelets wherein such inhibition may be for a patient suffering from a disease associated with the cardiovascular system.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0-300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of formula (1) of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula 1 or its pharmaceutical salt from about 0.1 to about 10% w/v (weight per unit volume).

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

It is understood herein that the following terms and (abbreviations) used herein are meant to be synonymous with each other: polymorphonuclear leukocytes (PMNL), [4-(2-hydroxyethyl)-1-piperazine-ethanesulfonic acid (HEPES), multiplicative factor of gravity used to express the centrifical force exerted during centrifugation ($\times$g), milliliters (mL), degrees centigrade (° C.), calcium ion ($Ca^{+2}$), nanometers (nm), dimethylsulfoxide (DMSO), ethylenebis(oxyethylenenitrilo)-tetraacetic acid (EGTA) grams (g), milligrams (mg), nanograms (ng), molar (M), millimolar (mM), micromolar (uM), opsonized zymozan (OZ), phorbol myristate acetate (PMA), formyl-methionyl-leucylphenylalanine (fMLP), leukotriene $B_4$ ($LTB_4$).

Compounds are often represented by a three letter abreviation "MDL" a space and a five or six digit extension. Therein it is understood the following representations: 1-phenyl-3-[3-(4-methoxybenzyloxy)phenyl]-2-propyne-1-one (MDL 100,225); 1-phenyl-3-(4-pyridinyl)-2-propyne-1-one (MDL 101,098); 1-(4-dimethylaminophenyl)-3-(4-pyridinyl)-2-propyne-1-one (MDL 102,175); 1-phenyl-3-[(4-benzyloxy)phenyl]-2-propyne-1-one (MDL 101,097); 1-(4-dimethylaminophenyl)-3-(4-pyridinyl)-2-propene-1-one (MDL 101,240); 1-phenyl-3-(4-pyridinyl)-2-propene-1-one (MDL 29,355); 1-(4-dimethylaminophenyl)-3-(4-pyrimidinyl)-2-propyne-1-one (MDL 102,387); 1-(4-dimethylaminophenyl)-3-(4-quinolindyl)-2-propyne-1-one (MDL 100,767); 1-(4-diethylaminophenyl)-3-(4-quinolinyl)-2-propyne-1-one (MDL 102,387).

The response of leukocytes to activation signals (stimulants) can be assessed by in vitro measurement of intracellular calcium or by measurement of released factors, such as superoxide anion, and myeloperoxidase. Further the response of leukocytes to stimulation in vivo can be assessed in animal models of edema, such as the mustard oil induced mouse ear edema model and the carrageenin induced rat paw edema model. Inventors of the present subject matter therein demonstrate the method of using the claimed compounds and their utility in the preceding assays.

Materials

Sprague-Dawley rats (150-250 grams) were from Harlan Sprague-Dawley (Indianapolis, Ind.). Hanks' balanced salts (HBSS; Gibco. Grand Island, NY) was supplemented with 20 mM HEPES and adjusted to pH 7.4. Sodium caseinate was from ICN Biochemical (Cleveland, Ohio). Fura-2/AM was from Molecular Probes (Eugene, Oreg.). Ionomycin was from Cal Biochem. (San Diego, Calif.). Superoxide dismutase was from DDI Pharmaceuticals (Mountain View, Calif.). All other reagents were from Sigma Chemical Co. (St. Louis, Mo.). All purchased reagents were used as received.

Isoaltion of Polymorphonuclear leukocvtes (PMNL)

Rat PMNL were obtained from exudates resulting from peritoneal injection of 6 mL of 8% sodium caseinate. Eighteen hours after injection rats were killed by carbon dioxide inhalation and the peritoneal cavity lavaged with Hank's balanced salt solution (HBSS).

After concentration of the PMNL by centrifugation, contaminating erythrocytes were removed by hypotonic lysis. The PMNL were then washed twice by centrifugation (400×g for 10 minutes) and resuspended in HBSS. Cell viability was greater than 90% by Trypan Blue exclusion and greater than 90% of the cells were PMNL by Wright-Giemsa stain.

Measurement of Intracellular Calcium

Intracellular calcium levels were obtained using Fura-2 as fluorescent indicator (Grynkiewicz et al., 1985). Fura-2 was loaded into PMNL as the acetoxymethyl ester (Fura-2/AM) using the method of Korchak et al., (1988). Specifically, $1 \times 10^8$ PMNL/mL were incubated in HBSS with 10 µM Fura-2/AM for 10 minutes at 37° C. The cells suspension was then diluted ten fold with HBSS and further incubated for another 20 minutes. The cells were then centrifuged (400×g for 8 minutes at 25° C.) and the PMNL ($1 \times 10^7$ cells/mL) resuspended in HBSS containing 1% bovine serum albumin. Cells were stored at room temperature and used within 3 hours.

Intracellular calcium level determinations were made using a dual wavelength spectrofluorometer (Photon Technology International, New Brunswick, N.J.). Two mL of PMNL suspension ($1 \times 10^7$ cells/mL) were stirred magnetically at 37° C. Cells were preincubated with the compounds for 15 minutes at 37° C. prior to activation. Where compounds were dissolved in DMSO and added directly, the DMSO never exceeded 0.3% in the final cell suspension. Total change in volume with addition of compounds or vehicle and stimuli never exceeded 3%. Intracellular calcium concentrations were calibrated by setting a maximum calcium level in the cells with the addition of 7 µM ionomycin to PMNL in HBSS containing 1% BSA. This was followed by treatment with 20 mM EGTA for 1 hour to obtain a minimum calcium level. The method of Grynkiewiez et al. (1985) was used to quantitate intracellular calcium levels, assuming $K_D$ for Fura-2 to be 240 nM. Each experiment was performed and repeated on three separate occasions and the pattern of calcium changes are representative of these experiments.

Myeloperoxidase (MPO) Release

MPO release was determined using the MPO catalyzed oxidation of o-dianisidine. The experiments were carried out in 96-well microtiter plates (Webster and Henson, 1978). In each well, 50 microliter (µl) aliquots of a PMNL suspension ($2 \times 10^7$ cell/mL in HBSS) were incubated with 50 µl of HBSS containing vehicle (0.3% DMSO) or inhibitor for 30 minutes at 37° C. The final DMSO concentration never exceeded 0.3% and was constant throughout each experiment. To activate the PMNL, 50 µl of one of the following were added for 30 minutes at 37° C.: N-formyl-Met-Leu-Phe (fMLP; 0.1 µM); phorbol myristate acetate (PMA, 200 ng/mL); or rat serum opsonized zymosan (OZ; 2.6 mg/mL, prepared by the method of Ward et al., 1983). The stimuli were added in 50 µl HBSS which also contained the compounds or vehicle, as appropriate, to avoid changing the inhibitor concentration. Cell activation was terminated by centrifugation of the plates at 600×g for 5 minutes at 22° C. Aliquots (100 µl) of supernatant were removed from each well and transferred to a 96-well flatbottomed microtiter plate for the MPO assay. To each aliquot of supernatant was added 100 µl of a freshly prepared solution containing 50 µl of 0.2M sodium phosphate buffer (pH 6.2), 25 µl of 3.9 mM O-dianisidine and 25 µl of 0.015 M hydrogen peroxide. Blanks were obtained using the same solution without hydrogen peroxide. The plates were mixed and then incubated at room temperature in the dark for about 15 minutes. Absorbances of the samples were measured at 450 nm.

Superoxide Anion (SOA) Production

Superoxide anion generation was measured using a method comparable to that of Leslie (1987) using microtiter plates, and carried out in presence of catalase (Arthur et al., 1987). Aliquots (50 µl) of a rat PMNL suspension ($2 \times 10^7$ cells/mL in HBSS) were incubated with 50 µl of HBSS containing vehicle (0.3% DMSO) or compound for 30 minutes at 37° C. as above. One hundred microliters of buffer containing 5.98 mg/mL of cytochrome C (Sigma Type III) and 0.1 mg/mL catalase, plus the compounds where appropriate, were then added to each sample. A blank for spectrophotometric measurement, containing unstimulated cells in the presence of cytochrome C, catalase and SOD, was also prepared. To activate the PMNL, 75 µl of PMA or OZ were added to achieve the final concentration of cell activator (plus vehicle or inhibitor as described above for MPO release) and the cells further incubated at 37° C. for 60 minutes. The activation was terminated by centrifugation at 600×g for 5 minutes at 4° C. Aliquots (200 µl) of supernatant were then transferred to a second, flat-well microtiter plate and measured spectrophotometrically at 550 nm.

EXAMPLE 10

Effect of Various Stimuli on PMNL Intracellular Calcium

Rat PMNL preloaded with Fura-2 were stimulated with fMLP and levels of intracellular calcium were followed (FIG. 1). The chemotactic peptide fMLP produced a biphasic response with a first peak reaching a maximum after 30 seconds and a second peak maximizing around 100 seconds after giving the peptide stimulus.

The biphasic response is consistent with those seen by Korchak et al., (1986) for human neutrophils wherein the peak of the response corresponds to an early release of intracellular calcium, as would be produced from a response with $LTB_4$. The second phase of the response, corresponding to the second peak at about 100 seconds after stimulation, is associated with an influx of extracellular calcium, typical from a Concanavalin A induced response. The biphasic response is interpreted by those skilled in the art to mean that the first phase is the release of intracellular calcium and the second phase corresponds to the influx of extracellular calcium.

EXAMPLE 11

Effect of compounds on Rat PMNL enzyme release and superoxide anion generation.

Rat PMNL were isolated in HBSS containing $Ca^{+2}$. As summarized in the figures below, fMLP stimulation of rat PMNL in the presence of cytochalasin B or with opsonized zymosan or with ionomycin results in the release of myeloperoxidase (fMLP/MPO, OZ/MPO, and ION/MPO; columns 2, 4, and 6 respectively). Addition of MDL 102,175 or MDL 101,098 showed a dose dependent inhibition of both responses at the given concentrations. Similarly, PMA and OZ results in superoxide anion production which is inhibited in a dose dependent fashion by the addition of MDL 102,175 or MDL 101,098 (PMA/SOA and OZ/SOA; columns 8 and 10 respectively). These data are also consistent with the affect that one would see if rat PMNL were deprived of extracellular calcium (data not shown).

grams) one hour prior to paw injection. Three hours following the carrageenin injection the difference in volume of the control and inflamed paw was measured. Each paw was immersed in a well of mercury and the volume of mercury displaced was recorded. Paws were uniformly dipped into the mercury up to the beginning

| 1 CONC (uM) MDL 102,175 | 2 IMLP/MPO | 3 SEM | 4 OZ/MPO | 5 SEM | 6 ION/MPO | 7 SEM | 8 PMA/SOA | 9 SEM | 10 OZ/SOA | 11 SEM |
|---|---|---|---|---|---|---|---|---|---|---|
| \multicolumn{11}{c}{EFFECT OF STIMULI ON MDL 102,175 INHIBITION OF RAT PMN MPO AND SOA} |
| 100 | 113.1 | 2.3 | 117.8 | 2.6 | 83.4 | 14.3 | 100.0 | 2.6 | 89.8 | 4.3 |
| 30 | 104.5 | 2.4 | 106.7 | 2.4 | 20.5 | 8.6 | 77.7 | 9.2 | 75.7 | 2.1 |
| 10 | 70.6 | 6.2 | 78.5 | 7.9 | 21.3 | 6.3 | 49.7 | 12.7 | 44.1 | 5.8 |
| 3 | 27.9 | 8.0 | 26.6 | 5.2 | 1.5 | 8.7 | 13.5 | 8.2 | 15.4 | 4.3 |
| 1 | 12.6 | 7.8 | 16.9 | 7.3 | 0.8 | 2.2 | −20.2 | 11.3 | −15.0 | 6.2 |

SEM is the standard error of the mean for the preceding numbered experiment.

| 1 CONC (uM) MDL 101,098 | 2 IMLP/MPO | 3 SEM | 4 OZ/MPO | 5 SEM | 6 ION/MPO | 7 SEM | 8 PMA/SOA | 9 SEM | 10 OZ/SOA | 11 SEM |
|---|---|---|---|---|---|---|---|---|---|---|
| \multicolumn{11}{c}{EFFECT OF STIMULI ON MDL 101,098 INHIBITION OF RAT PMN MPO AND SOA} |
| 100 | 96.2 | 1.8 | 97.2 | 4.5 | 88.4 | 4.1 | 97.2 | 2.3 | 115.0 | 10.1 |
| 30 | 80.8 | 9.0 | 92.2 | 1.1 | 12.7 | 2.7 | 70.0 | 10.3 | 61.5 | 8.3 |
| 10 | 34.9 | 5.7 | 48.7 | 8.6 | 5.7 | 2.5 | 29.1 | 5.8 | 20.3 | 5.0 |
| 3 | 7.5 | 6.1 | 14.7 | 7.7 | 0.0 | 1.3 | −4.3 | 10.6 | −7.5 | 6.6 |
| 1 | 2.9 | 4.4 | 5.4 | 10.9 | −2.8 | 0.7 | −30.7 | 7.9 | −18.0 | 3.9 |

SEM is the standard error of the mean for the preceding numbered experiment.

EXAMPLE 12

Mustard Oil-Induced Mouse Ear Edema

Charles River male CD-1 mice weighing 30–60 grams were divided into randomized groups. They were dosed i.p. for 30 minutes prior or orally 1 hour prior to application of 20 μl of mustard oil (10% isothiocyanate in acetone) to the right ear. After 30 minutes the mice were sacrificed and an 8 millimeter diameter circular punch biopsy of each ear was obtained and weighted. The difference between the left (control) and right (treated) ear weights were expressed as percent increase. Results of the Mustard Oil Induced Mouse Ear Edema Test are shown in the table below.

| \multicolumn{4}{c}{MUSTARD OIL INDUCED MOUSE EAR EDEMA} |
|---|---|---|---|
| COMPOUND | DOSE (mg/Kg) | Route | % Inhibition |
| MDL 101,098 | 100 | i.p. | 68.2 ± 5.8 |
|  | 30 |  | 56.8 ± 6.4 |
|  | 10 |  | 38.6 ± 13.1 |
| MDL 101,098 | 100 | oral | 43.9 ± 15.6 |
|  | 30 |  | 6.4 ± 27.7 |
|  | 10 |  | 38.5 ± 34.9 |
| MDL 102,175 | 100 | i.p. | 68.2 ± 5.8 |
|  | 30 |  | 56.8 ± 6.4 |
|  | 10 |  | 38.6 ± 13.1 |
| MDL 102,175 | 100 | oral | 43.9 ± 15.6 |
|  | 30 |  | 6.4 ± 27.7 |
|  | 10 |  | 38.5 ± 34.9 |

EXAMPLE 13

Carrageenin-Induced Rat Paw Edema

Charles River male Sprague-Dawley rats weighing 90 to 100 grams were used. Inflammation of the left hind paw was induced by a 1% carrageenin solution (0.05 cc), injected into the plantar surface of the paw. The contralateral paw was injected with an equal volume of saline. Drugs were administered orally or i.p. (1 cc/100 grams) one hour prior to paw injection. Three hours following the carrageenin injection the difference in volume of the control and inflamed paw was measured. Each paw was immersed in a well of mercury and the volume of mercury displaced was recorded. Paws were uniformly dipped into the mercury up to the beginning of the hairline. A venous pressure transducer, coupled to a chart recorder, was employed to measure the small volumes of mercury displaced. Each group measurement consists of the average of four rats, each with three separate measurements. Results of the Carrageenin Induced Rat Paw Edema test are shown in the table below.

| \multicolumn{3}{c}{CARRAGEENIN INDUCED RAT PAW EDEMA} |
|---|---|---|
| Compounds | Route | % Inhibition |
| MDL 101,098 | p.o | 42.4 |
| MDL 102,175 | p.o. | 19.8 |
| MDL 101,098 | i.p. | 64.8 |
| MDL 102,175 | i.p. | 73.2 |

What is claimed is:

1. A compound of the formula:

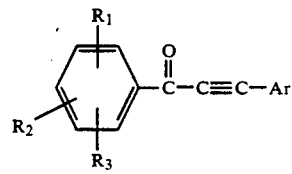

(1)

wherein
$R_1$, $R_2$ and $R_3$ each time taken are independently hydrogen; $C_1$–$C_6$ alkyl; $C_1$–$C_6$ alkoxy; halogen; —$N(Y_1)(Y_2)$, wherein $Y_1$ and $Y_2$ are each independently hydrogen or $C_1$–$C_6$ alkyl; or $X_z$—(Q)—(CH$_2$)$_n$—O—, wherein Q is phenyl or naphthyl, $n=0$ or 1, $X = C_1$–$C_6$ alkoxy or —$N(Y_1)(Y_2)$, wherein $Y_1$ and $Y_2$ are as defined previously, and $Z=0, 1, 2$;
wherein Ar is a radical of the formulae:

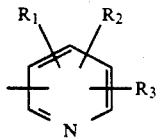

or a pharmaceutically acceptable salt thereof.

2. A compound of claim 1 wherein the compound is 1-(4-dimethylaminophenyl)-3-(4-pyridinyl)-2-propyne-1-one.

3. A compound of claim 1 wherein the compound is 1-phenyl-3-(4-pyridinyl)-2-propyne-1-one.

4. A compound of claim 1 wherein the compound is 1-phenyl-3-(3-pyridinyl)-2-propyne-1-one.

5. A compound of claim 1 wherein the compound is 1-(4-diethylaminophenyl)-3-(4-pyridinyl)-2-propyne-1-one.

6. A method for inhibiting calcium uptake in platelets in a patient in need thereof comprising administering to said patient an effective calcium uptake inhibitory amount of a compound of claim 1.

7. A method according to claim 6 wherein the patient is suffering from a cardiovascular disorder.

8. A method according to claim 6 wherein the patient is suffering from myocardial infarction.

9. A method according to claim 6 wherein the patient is suffering from an ischemic reperefusion injury.

* * * * *

UNITED STATES PATENT AND TRADEMARK OFFICE
CERTIFICATE OF CORRECTION

PATENT NO. : 5,223,518

DATED : June 29, 1993

INVENTOR(S) : Robert J. Dinerstein, Jeffrey S. Sabol, Keith A. Diekema

It is certified that error appears in the above-identified patent and that said Letters Patent is hereby corrected as shown below:

Column 1, line 6 the patent reads: "filed Oct. 11, 1990, continuation-in-part of", and should read --filed Oct. 11, 1990, which is a continuation-in-part--.

Column 1, line 12 the patent reads "pharma-ceutical", and should read --pharmaceutical--.

Column 1, line 35 the patent reads "extracellar", and should read --extracellular--.

Column 1, line 46 the patent reads "distinquished", and should read --distinguished--.

Column 2, line 10 the patent reads "is not known it is clear", and should read --is not known, it is clear--.

Column 3, line 30 the patent reads "Y2 are each", and should read --Y2 each time taken are--.

Column 4, line 17 the patent reads "one one to six", and should read --one to six--.

Column 5, line 16 the patent reads "can be remove", and should read --can be removed--.

Column 5, line 47 the patent reads "be means", and should read --by means--.

Column 5, line 52 the patent reads "chloride", and should read --chloride.--

Column 9, line 5 the patent reads "diethyl-amine", and should read --diethylamine--.

UNITED STATES PATENT AND TRADEMARK OFFICE
CERTIFICATE OF CORRECTION

PATENT NO. : 5,223,518

DATED : June 29, 1993

INVENTOR(S) : Robert J. Dinerstein, Jeffrey S. Sabol, Keith A. Diekema

It is certified that error appears in the above-identified patent and that said Letters Patent is hereby corrected as shown below:

Column 9, line 48 the patent reads "amd recrystallize", and should read --and recrystallize--.

Column 9, line 55 the patent reads "[((4-Quinolinyl)", and should read --[(4-Quinolinyl)--.

Column 10, line 58 the patent reads "tetrhydrofuran", and should read --tetrahydrofuran--.

Column 14, line 9 the patent reads "interchangably", and should read --interchangeably--.

Column 15, line 60 the patent reads "the these", and should read --these--.

Column 16, line 11 the patent reads "a inflammatory", and should read --an inflammatory--.

Column 16, line 19 the patent reads "there exist", and should read --there exists--.

Column 16, line 39 the patent reads "the the", and should read --the--.

Column 17, line 11 the patent reads "an events that lead", and should read --an event that leads--.

Column 17, line 28 the patent reads "a effective", and should read --an effective--.

Column 17, line 33 the patent reads "a immune", and should read --an immune--.

UNITED STATES PATENT AND TRADEMARK OFFICE
CERTIFICATE OF CORRECTION

PATENT NO. : 5,223,518

DATED : June 29, 1993

INVENTOR(S) : Robert J. Dinerstein, Jeffrey S. Sabol, Keith A. Diekema

It is certified that error appears in the above-identified patent and that said Letters Patent is hereby corrected as shown below:

Column 17, line 50 the patent reads "a effective", and should read --an effective--.

Column 17, line 63 the patent reads "a immune", and should read --an immune--.

Column 18, line 12 the patent reads "(nag", and should read --(mg--.

Column 18, line 42 the patent reads "a effective" and should read --an effective--.

Signed and Sealed this

Twelfth Day of September, 1995

Attest:

BRUCE LEHMAN

Attesting Officer    Commissioner of Patents and Trademarks